(12) United States Patent  
Carpenter

(10) Patent No.: US 7,976,529 B2  
(45) Date of Patent: Jul. 12, 2011

(54) HIGH FLOW VOLUME NASAL IRRIGATION DEVICE AND METHOD FOR ALTERNATING PULSATILE AND CONTINUOUS FLUID FLOW

(75) Inventor: Mark Carpenter, White Lake, MI (US)

(73) Assignee: Skylab Developments Inc., White Lake, MI (US)

( * ) Notice: Subject to any disclaimer, the term of this patent is extended or adjusted under 35 U.S.C. 154(b) by 0 days.

(21) Appl. No.: 12/941,056

(22) Filed: Nov. 6, 2010

(65) Prior Publication Data

US 2011/0087194 A1    Apr. 14, 2011

Related U.S. Application Data

(63) Continuation-in-part of application No. 12/900,792, filed on Oct. 8, 2010.

(60) Provisional application No. 61/280,695, filed on Nov. 9, 2009, provisional application No. 61/337,779, filed on Feb. 12, 2010, provisional application No. 61/280,696, filed on Nov. 9, 2009.

(51) Int. Cl.
  *A61M 31/00* (2006.01)
  *A61M 1/00* (2006.01)
  *B05B 1/08* (2006.01)
  *F15C 1/08* (2006.01)

(52) U.S. Cl. ........ 604/516; 604/34; 137/826; 239/102.1

(58) Field of Classification Search .............. 604/27, 604/31, 34, 37, 48, 500, 514, 516, 94.01, 604/118, 132, 185, 186, 245, 256, 257; 239/101, 239/102.01; 137/826; 222/92, 96
See application file for complete search history.

(56) References Cited

U.S. PATENT DOCUMENTS

| | | | | |
|---|---|---|---|---|
| 2,483,661 | A * | 10/1949 | Neas | 222/4 |
| 2,590,215 | A * | 3/1952 | Sausa | 138/45 |
| 3,211,349 | A * | 10/1965 | Prussin et al. | 222/402.18 |
| 3,469,582 | A * | 9/1969 | Jackson | 604/119 |
| 3,883,074 | A * | 5/1975 | Lambert | 239/101 |
| 4,417,861 | A * | 11/1983 | Tolbert | 417/315 |
| 4,489,750 | A * | 12/1984 | Nehring | 137/496 |
| 4,642,833 | A * | 2/1987 | Stoltz et al. | 15/1.7 |
| 5,195,664 | A | 3/1993 | Rhea | |
| 5,381,961 | A * | 1/1995 | Evans et al. | 239/333 |
| 5,819,801 | A * | 10/1998 | Palffy | 137/826 |
| 5,899,878 | A * | 5/1999 | Glassman | 604/48 |
| 6,125,843 | A * | 10/2000 | Gold et al. | 128/200.23 |
| 6,669,059 | B2 | 12/2003 | Mehta | |
| 2011/0087174 | A1 * | 4/2011 | Carpenter | 604/257 |
| 2011/0087188 | A1 * | 4/2011 | Carpenter | 604/500 |

* cited by examiner

*Primary Examiner* — Theodore Stigell  
*Assistant Examiner* — Andrew Gilbert  
(74) *Attorney, Agent, or Firm* — Lyman H. Moulton, Esq.

(57) ABSTRACT

A high flow volume nasal irrigation device for alternating pulsatile and continuous fluid flow includes a segmented dip tube with a free end extending inside a squeeze bottle configured to convey a liquid under an elevated chamber pressure from a reservoir therein to a lower pressure outside the bottle. The device also includes an elastic segment at the free end of the tube configured to oscillate about a bending in the segment in response to a differential pressure between an internal pressure and the chamber pressure, the segment having an elastic restoring force in opposition to the bending. The disclosed device further includes a pulsatile portion of the elastic segment configured to close at the segment bending and to reopen under the elastic restoring force and to thus generate a periodic pulsatile fluid flow through the tube with a period corresponding to the elastic segment oscillation.

20 Claims, 12 Drawing Sheets

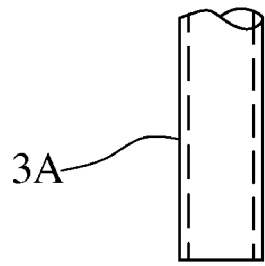
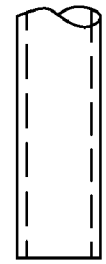
FIG. 4A
FIG. 4C
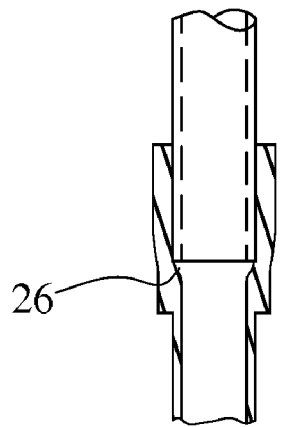
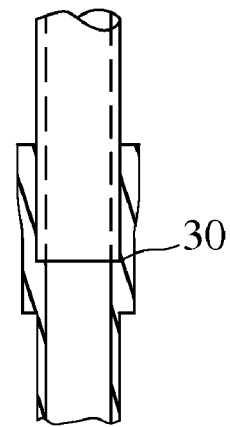
FIG. 4B
FIG. 4D

HIGH FLOW VOLUME NASAL IRRIGATION DEVICE AND METHOD FOR ALTERNATING PULSATILE AND CONTINUOUS FLUID FLOW

CROSS-REFERENCE TO RELATED APPLICATIONS

This application is a continuation-in-part of U.S. patent application Ser. No. 12/900,792 entitled A High Flow Volume Nasal Irrigation Device and Method for Alternating Pulsatile and Continuous Fluid Flow, filed for Mark Carpenter on Oct. 8, 2010 incorporated herein by reference in its entirety. This application incorporates herein by reference in its entirety each earlier filed U.S. Provisional Patent Application Ser. No. 61/280,695 entitled High Volume Nasal Irrigation Device with Pulsatile Flow—Version 2, filed Nov. 9, 2009, for Mark Carpenter and U.S. Provisional Patent Application Ser. No. 61/337,779 entitled High Volume Nasal Irrigation Device with Pulsatile Flow—Version 2b, filed Feb. 12, 2010, for Mark Carpenter and U.S. Provisional Patent Application Ser. No. 61/280,696 entitled High Volume Nasal Irrigation Device with Pulsatile Flow—Version 3, filed Nov. 9, 2009, also for Mark Carpenter.

BACKGROUND AND FIELD OF INVENTION

Flood irrigation differs significantly from the practice of inhaling an atomized mist into the nose. During flood irrigation, the vast majority (>95%) of fluid taken in is expelled immediately (or shortly thereafter) after the contaminants have been rinsed out. Rinsing with flood irrigation is commonly performed by ingesting the liquid solution into one nostril and concurrently expelling the solution from the other nostril. Alternately, flood irrigation is sometimes performed by ingesting the liquid solution into both nostrils simultaneously and having the excess flow to the mouth. Flood irrigation has been demonstrated to be more effective than mist for the distribution of medications and the physical rinsing of the mucus membranes of the nose and sinuses. A user of nasal flood irrigation may typically use the technique once or twice per day as opposed to a user applying a mist several to many times a day.

The use of flood irrigation to cleanse, soothe and rehabilitate nasal and sinus passages has a long history which probably began with the practice of intentional inhalation of sea water from cupped hands. Later devices such as the Neti Pot made the practice more practical. Today there is a wide array of devices and technologies to facilitate the rinsing by flood irrigation of the nasal passages and sinus cavities. Investigation of prior art shows that the number of relevant devices and techniques has grown at an increasing rate in recent decades and in particular during the last ten years. This growth in technology has paralleled the increasing popularity of the practice as the technology has become more effective and as the benefits of the practice have become more appreciated.

Within the field of flood irrigation for nasal rinsing there are developments in the liquid solutions being used and there are developments in the device which delivers the liquid stream. The liquid delivery devices for nasal flood irrigation may be generally divided into two major commercial categories—a) simple devices which dispense a continuous low pressure stream of fluid from a squeeze bottle, deformable bulb, bellows container, shower head connection, gravity feed, etc., and b) devices which use a motorized pump or other complex and expensive electromechanical apparatus to provide a pulsating stream of fluid. Both categories of device have advantages and disadvantages.

The devices which dispense a continuous low pressure stream of irrigant typically are very low in cost and may have advantageously high flow rate capability. Unfortunately, these devices offer a less than optimal cleaning ability due to the tendency of the continuous stream to form laminar flow paths across the surfaces to be rinsed and due to the surfaces not being deformed and agitated by the smooth flow stream. These continuous stream devices are also ineffectual in projecting liquid medications or irrigants into sinus cavities because the closed end cavities require time varying pressures to cause fluid entry. They also fail to rehabilitate nasal cilia which have lost motility.

The pulsating electromechanical devices have the advantages of causing a much more turbulent scouring flow with high shear stress gradients along the surfaces, causing a mixing action to reduce surface based concentration gradients and deformations of the surfaces being rinsed (for flexible surfaces) and healthy movement of the nasal cilia. Pulsating electromechanical devices unfortunately offer a less than optimal flow rate. Additionally, the pulsatile electromechanical devices are significantly more complex and costly, with purchase cost approximately ten times that of a squeeze bottle irrigator. This high cost prevents many potential users from purchasing them and does not favor the periodic disposal of the device which is necessary to avoid colonization by bacteria and molds.

SUMMARY OF THE INVENTION

A high flow volume nasal irrigation device for alternating pulsatile and continuous fluid flow is disclosed which includes a segmented dip tube with a free end extending inside a squeeze bottle configured to convey a liquid under an elevated pressure within the bottle from a reservoir therein to a lower pressure outside the bottle. The device also includes an elastic segment configured at the free end of the tube configured to oscillate about a bending in the segment in response to a differential pressure between an internal pressure and the applied pressure, the segment having an elastic restoring force in opposition to the bending. The disclosed device further includes a pulsatile portion of the elastic segment configured to close at the segment bending and to reopen under the elastic restoring force and to thus generate a periodic pulsatile fluid flow through the tube, a pulsatile fluid flow period corresponding with the elastic segment oscillation. The dip tube free end also comprises an inlet structure configured to generate an initial fluid pressure drop across the structure to locate the pulsatile portion in the elastic segment and prevent the end from collapsing. Also, an end of the elastic segment is configured into a socket to receive the dip tube in a stretched fit connection where a portion of the socket proximal to the segment is configured to have a pocket of inside diameter larger than an inside diameter of another portion of the socket distal to the segment. A removable cap on the bottle comprises an orifice and a bore coaxial with the orifice configured to an outside diameter of the dip tube to allow the orifice diameter to match the inside diameter of the dip tube.

A method for high flow volume nasal irrigation with alternating pulsatile and continuous fluid flows is disclosed which includes oscillating an elastic segment of the dip tube free end about a bending of the segment by squeezing the bottle and applying a differential pressure between an internal pressure and the chamber pressure on the dip tube. The method also includes closing and reopening a pulsatile portion of the dip tube at the bending in the elastic segment in response to the differential pressure and an elastic restoring force in opposition to the bending. The method further includes providing a pulsatile fluid flow through the bottle cap orifice and into the user's nostril, the pulsatile flow in response to the oscillating segment and the closing and reopening of the pulsatile portion, a pulsatile period and the segment oscillation corresponding with a pressure threshold constant. The disclosed method further comprises squeezing the bottle gently to a chamber pressure below the pressure threshold constant to eject a continuous stream of the fluid from the bottle and squeezing the bottle vigorously to a chamber pressure above the pressure threshold constant to eject an oscillatory pulsating stream of the fluid from the bottle. The method also further comprises alternating between ejecting a continuous fluid stream and a pulsating fluid stream by alternating the respective gentle and vigorous squeezings. The method also allows varying an oscillatory frequency of a pulsating stream of fluid ejected from the bottle by varying the manual pressure applied to the squeeze bottle.

BRIEF DESCRIPTION OF THE DRAWINGS

FIG. 4A is a cross-sectional view of a straight walled socket taken through the diameter of the elastic segment in accordance with an embodiment of the present disclosure.

FIG. 4B is a cross-sectional view of the straight walled socket after the tube segment 3A is inserted therein in accordance with an embodiment of the present disclosure.

FIG. 4C is a cross-sectional view of a pocket socket taken through the diameter of the elastic segment in accordance with an embodiment of the present disclosure.

FIG. 4D is a cross-sectional view of the pocket socket after the tube segment 3A is inserted therein in accordance with an embodiment of the present disclosure.

Figure 1:
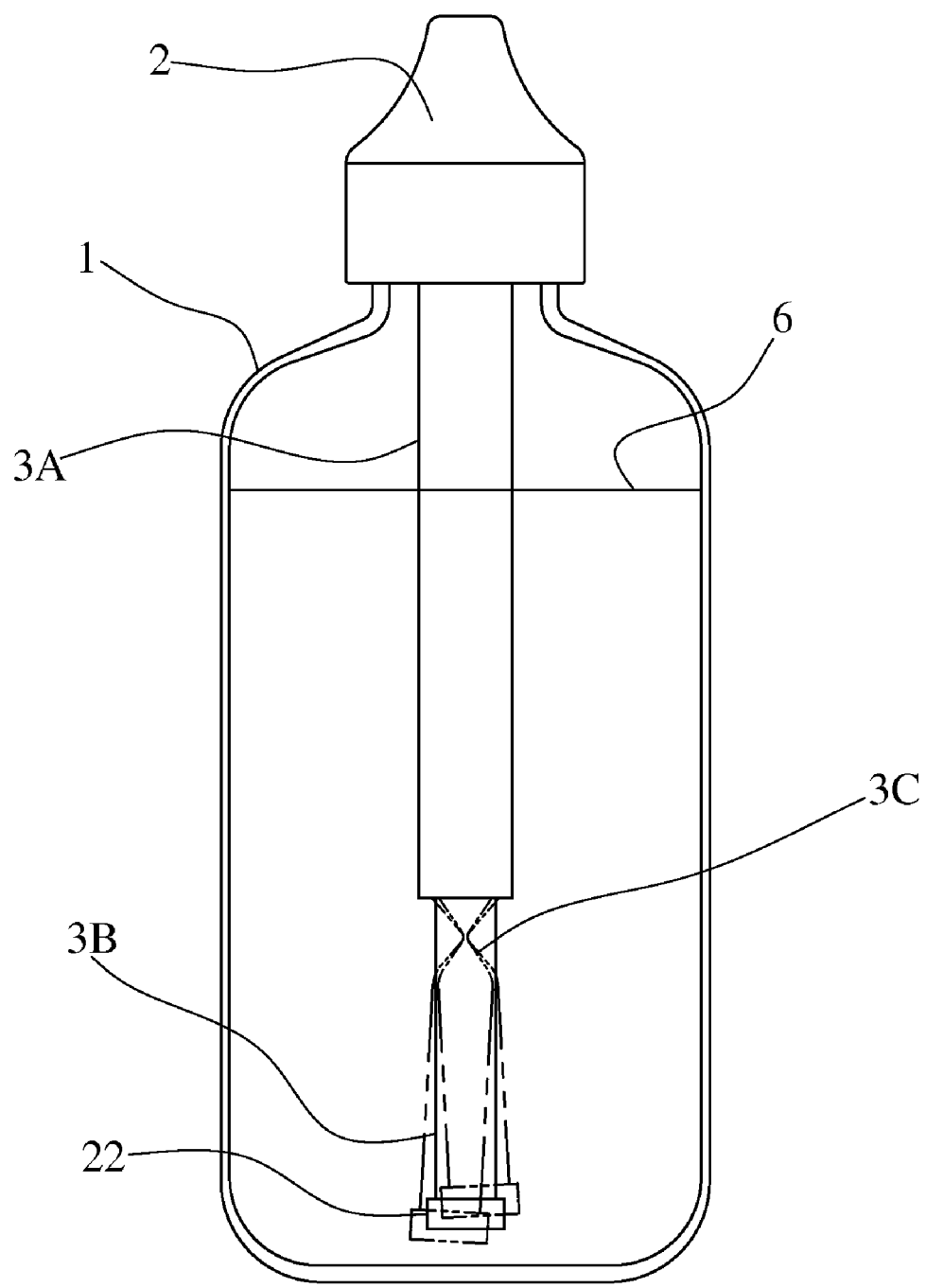
FIG. 1 is a side elevational view of a high flow volume nasal irrigation device for alternating pulsatile and continuous fluid flow in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

The disclosed device is capable of providing a continuous flow rate from gentle to very high flow and alternatively at the control of the user, capable of generating a strong pulsatile flow stream at a variable intensity, amplitude and frequency. The disclosed device also may be priced similar to bottle based devices, is simple to manufacture, easy to clean and maintain and is disposable.

The pulse generating mechanism consists of an elastic segment of a segmented dip tube in which the wall thickness has been reduced to the point of becoming substantially flexible. During use, high fluid flow velocities through this segment of tube cause the pressure within the tube to be lower than the pressure acting on the exterior of the tube (Bernoulli's law). At sufficiently high flow velocities the pressure differential will exceed a critical value (the hoop stress buckling limit of the thinned section of the tube) causing the walls of a pulsatile portion of the flexible section to collapse and bend the elastic segment momentarily to shut off flow at the pulsatile portion of the tube segment. Once a bending event is initiated, the free end of the tube moves through the fluid in the reservoir in response to the bending. Rapid and full closure of the tube is then assured due to the combined effects of increasing flow velocity driven by the reduction in flow area and due to the loss of tube wall strength caused by bending. The resulting closure of the flow path stops flow within the tube. With fluid flow stopped, fluid pressure within the tube once again equalizes with fluid pressure external to the tube allowing the hoop stress in the elastomeric tube to predominate and re-open the tube to its original cross section at a predetermined bending location. The elastic segment thus oscillates back and forth within the fluid in the reservoir as the pulsatile portion periodically closes and reopens.

Assuming the user maintains adequate squeeze pressure on the bottle, flow will re-initiate and the liquid flow velocity will again increase to a level sufficient to cause closure of the tube. This process repeats to create a continuing on/off/on . . . pulsation in the liquid stream delivered by the device. In practice the tube bends and stops flow at the same pulsatile portion of the tube segment on every cycle and the closure position does not move along the tube length or form multiple waves. The point of closure is determined by many design factors of the present disclosure including dip tube length, tube wall geometry and strength, pulsatile portion distance from tube end, and tube inlet flow geometry as explained and detailed below.

FIG. 1 is a side elevational view of a transparent high flow volume nasal irrigation device for alternating pulsatile and continuous fluid flow in accordance with an embodiment of the present disclosure. Though the device depicted is transparent to facilitate illustrating elements of the claimed disclosure, other embodiments may include any combination of translucent and opaque elements. The device as depicted may include a deformable chamber or bottle 1, a removable cap 2 and a segmented dip tube including segment 3A, an elastic segment 3B and a pulsatile portion 3C, an inlet structure 22 and a reservoir of fluid 6.

The segmented dip tube is arranged with a free end extending inside the chamber 1 and another end extending outside the chamber 1. The chamber 1 may be an elastically deformable enclosed space such as a squeeze bottle. The dip tube is designed to convey a liquid from the reservoir 6 in the chamber 1 under an elevated chamber pressure to a lower pressure outside the chamber 1. An elevated pressure may be generated by a gentle buildup of a pressure difference inside the bottle 1 with respect to the chamber exterior or it may be generated by a vigorous squeezing motion on the chamber 1 by a user's thumb and fingers. The dip tube may provide a continuous fluid flow from the inlet reinforcing structure 22 to the elastic segment 3B to the pulsatile portion 3C. The tube segment 3A may be semi-rigid in order to direct the elastic segment 3B toward the extremities of the reservoir 6.

The elastic segment 3B may comprise a lower durometer material than the rest of the dip tube. The elastic segment 3B may be a nominal length of 35 mm or 1.4 inches. The elastic segment 3B oscillates about a bending of the segment 3B at the pulsatile portion 3C in response to a differential pressure between an internal pressure and the applied pressure. The segment 3B has an elastic restoring force in opposition to the bending. Therefore, the free end of the elastic segment 3B may oscillate back and forth in an arc about the bending at the pulsatile portion 3C or it may oscillate up and down about the bending.

The pulsatile portion 3C of the elastic segment 3B may comprise same or similar durometer materials as the elastic segment 3C. The pulsatile portion 3C is specifically designed to generate a pulsatile fluid flow from a collapse or closing of the portion 3C under the pressure differential from the fluid velocity through the elastic segment 3B. The fluid velocity of the liquid through the elastic segment 3B in response to the applied pressure creates a negative pressure difference on an internal surface of the pulsatile portion 3C with respect to its outside surface. This differential pressure causes the pulsatile portion 3C to close or collapse. The pulsatile portion 3C also reopens under an elastic restoring force intrinsic to the elastic segment 3B in combination with a reduction in the fluid velocity which decreases the differential pressure on the pulsatile portion 3C. The closing and reopening of the pulsatile portion 3C continues as the fluid velocity and associated differential pressures fluctuate until there is no more fluid moving through the elastic segment 3B from the reservoir 6 or the user may relax his or her grip to allow a continuous flow. A period of the pulsatile fluid flow through the tube 3A corresponds to the elastic segment 3B oscillation about the bending of the segment 3B. Also, a length of the pulsatile portion 3C along the elastic segment 3B may be substantially equal to the inside diameter of the elastic segment 3B. Additionally, a wall thickness of the elastic segment may extend only for a length between 1 and 10 times an inside diameter of the segment. Furthermore, as depicted in FIG. 1, the pulsatile portion may close or collapse in a pinch-off of the tube near the radial center of the elastic segment 3B.

An embodiment of the device further comprises a predetermined location for the bending of the elastic segment 3B where the differential pressure across the segment 3B exceeds a hoop stress buckling limit of the segment 3B and closes the pulsatile portion 3C, the differential pressure determined in part by a decrease of the internal pressure in the segment 3B resulting from an elevated fluid velocity therein. Also the pulsatile portion 3C is configured to reopen to its original cross section at a predetermined bending location with a period corresponding to the elastic segment oscillation where the elastic restoring force intrinsic to the portion 3C configuration overcomes the differential pressure across the segment 3B, the differential pressure determined in part by an increase of the internal pressure in the segment 3B resulting from a decrease of the fluid velocity therein.

An embodiment of the disclosed high flow volume nasal irrigation device may include a first substantially rigid segment of the tube 3A positioned adjacent a chamber 1 opening and a second substantially rigid segment of the tube positioned adjacent the extended free end in the chamber 1. The elastic segment 3B in such an embodiment may be positioned between the first and second substantially rigid segments. The second substantially rigid segment of the tube 3B may include an inlet structure 22 described below.

Figure 2:
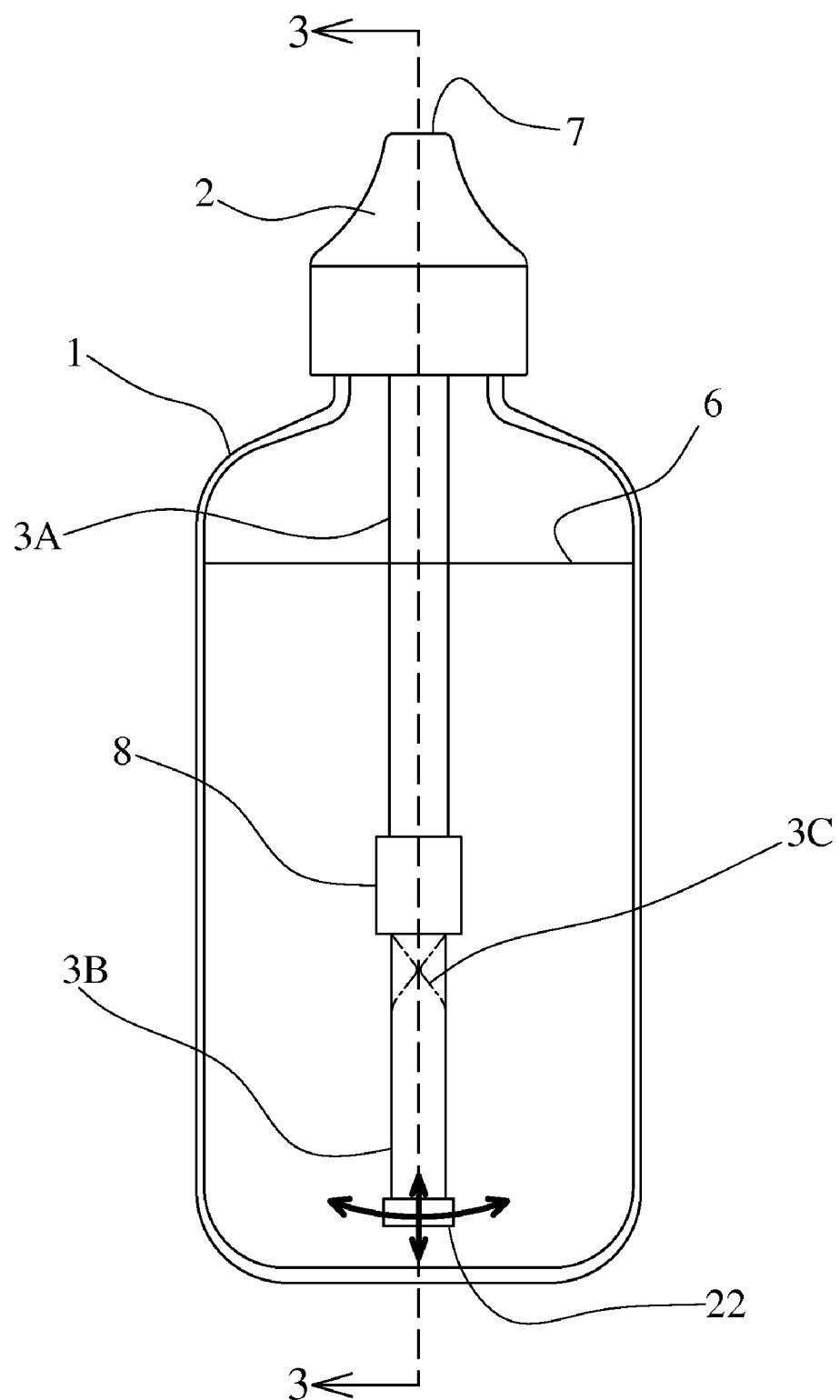
FIG. 2 is a side elevational view of a commoditized high flow volume nasal irrigation device for alternating pulsatile and continuous fluid flow, with B showing oscillation, in accordance with a disclosed embodiment.
Figure 3:
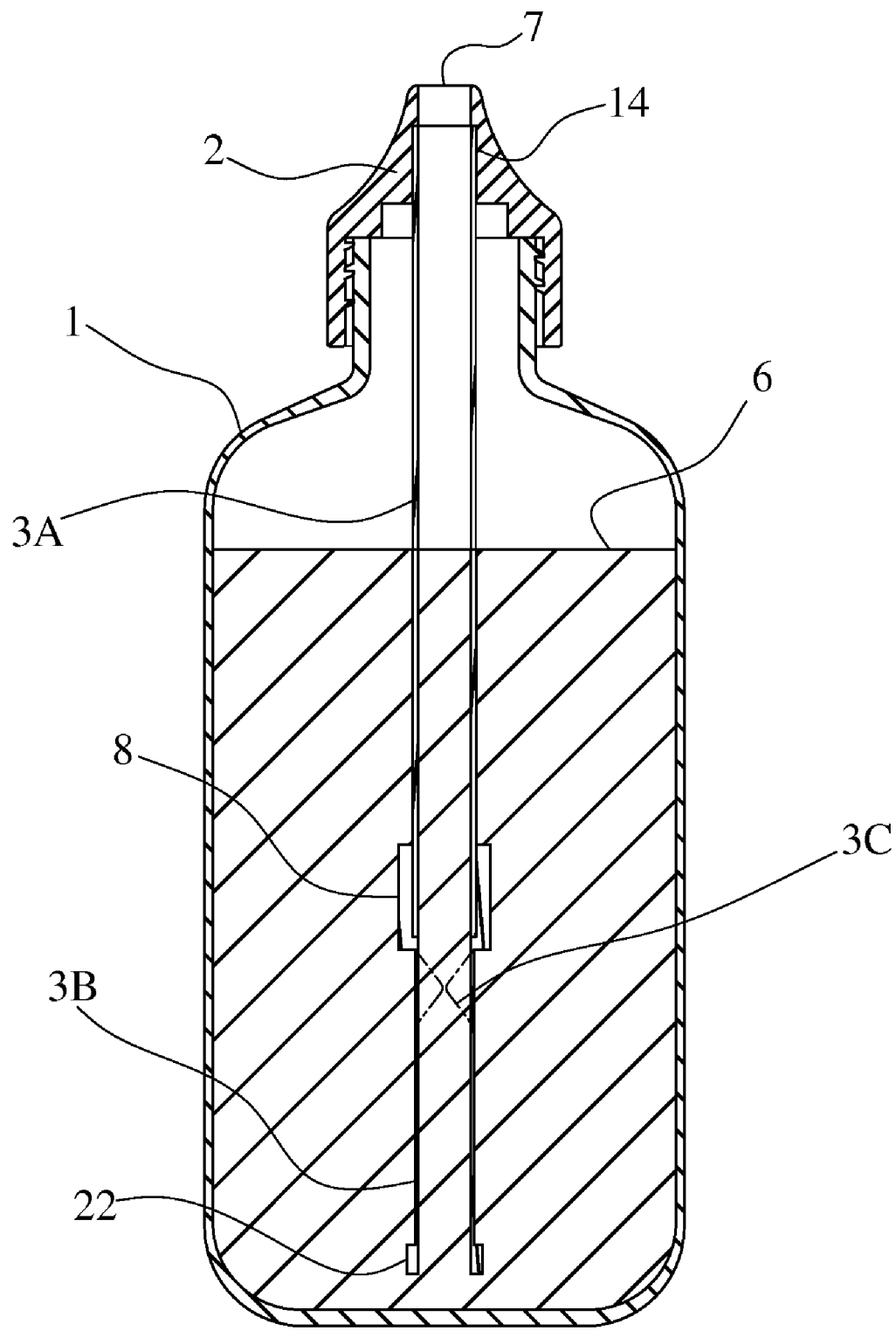
FIG. 3 is a cross-sectional view of the commoditized high flow volume nasal irrigation production device of FIG. 2 taken through the diameter of the device in accordance with an embodiment of the present disclosure.

FIG. 2 is a side elevational view of a commoditized high flow volume nasal irrigation production device for alternating pulsatile and continuous fluid flow in accordance with an embodiment of the present disclosure. Again, the device depicted is transparent, but other embodiments may include a combination of translucent and opaque elements. The device depicted includes a squeeze bottle chamber 1, a removable cap 2, a segmented dip tube comprising a segment 3A, an elastic segment 3B and pulsatile portion 3C, an inlet structure 22, a liquid reservoir 6, a cap orifice 7 and a socket 8. Cross section 3-3 is shown in FIG. 3 below. Arrows indicate oscillatory movement back and forth, up and down.

FIG. 3 is a cross-sectional view of the commoditized high flow volume nasal irrigation production device of FIG. 2 taken through the diameter of the device in accordance with an embodiment of the present disclosure. The production device in cross section includes the same numbered elements as depicted in FIG. 2. However, details of the interior of the cap 2 are also shown including the orifice 7 and the coaxial bore 14. Also, as explained below with respect to FIG. 4, details of the socket 8 are further shown.

The dip tube may have a smooth and substantially consistent inside diameter from a first tube end to a second tube end and throughout the full length of the tube 3 during a continuous fluid flow state. The first tube end is arranged to extend into the squeeze bottle 1 interior and the second tube end to extend outside the squeeze bottle chamber 1. Segments of the dip tube may comprise semi-rigid materials or comprise a thick wall material to give it semi-rigid properties.

The squeeze bottle 1 is designed and may be made to elastically deform in response to a manual pressure from a user. The squeeze bottle 1 may comprise an open end and an interior. The squeeze bottle 1 may also be comprised of an elastic thin-wall LDPE (low-density polyethylene) material in order to minimize the squeeze pressure needed to create the pulsatile flow in the pulsatile portion 3C of the elastic segment 3B. The squeeze bottle 1 may be configured to fit comfortably into the grasp of an average person and be deformed in response to an average person's squeezing grip. The squeeze bottle 1 therefore may also elastically resume its original shape in preparation for repeated filling and additional use.

The elastic segment 3B of the dip tube may be coaxial with the dip tube and extend further into the squeeze bottle 1 interior in order to pick up fluid from the extremities of the reservoir 6. A pulsatile portion 3C of the elastic segment 3B is designed and made to generate a periodic pulsatile fluid flow from a collapse of the portion 3C under a pressure differential between an internal pressure and the elevated chamber pressure. The pulsatile portion 3C is also designed and made to reopen in response to an elastic restoring force intrinsic to the elastic segment 3B in combination with a reduction in the fluid velocity. The elastic segment 3B may therefore be comprised of an elastomeric deformable material having a low durometer.

In an embodiment of the present disclosure, the elastic segment 3B may comprise a 6 mm (0.24 inches) nominal inside diameter and is no smaller than 3 mm (0.12 inches) in diameter and no greater than 8 mm (0.32 inches) in diameter.

In another embodiment of the present disclosure, the elastic segment 3B may comprise a wall thickness no smaller than 0.15 mm (0.006 inches) and no greater than 0.69 mm (0.027 inches). In an embodiment of the high flow volume nasal irrigation device of the present disclosure, a wall thickness of the elastic segment 3B extends only for a length between 1 to 10 times an inside diameter of the segment. The elastic segment 3B is further configured to collapse when subjected to an externally applied pressure differential of 2.07 kPa (0.3 psi) to 13.80 kPa (2.0 psi) and return to its original form when the pressure differential is reduced to less than 1.72 kPa (0.25 psi).

A removable cap 2 may be arranged on the squeeze bottle 1 open end. It may comprise an exterior adapted to seal against a user's nostril. The cap 2 may also comprise a threaded inside diameter corresponding to the outside threaded diameter of the squeeze bottle 1 opening. The cap 2 may also comprise an orifice 7 and a bore 14 coaxial with the orifice. The bore 14 is designed and made to have a diameter large enough to receive the outside diameter of the dip tube segment 3A and yet allow the inside diameter of the dip tube to match the diameter of the orifice 7. Therefore, the dip tube may maintain a constant and consistent diameter from the inlet end of the tube 22 through the full length of the tube to the outlet of the tube at the orifice 7 of the cap 2 in a continuous flow state. Therefore, with the exception of the pulsatile portion 3C of the tube, the constant and continuous diameter of the tube may also maximize flow rate and pulsation strength in the active pulsatile state.

Embodiments of the disclosed high flow volume nasal irrigation production device may include an inlet structure 22 on the dip tube free end configured to generate an initial and predetermined fluid pressure drop across the inlet 22 to locate the pulsatile portion 3C in the elastic segment and to prevent the tube inlet from collapsing in response to the fluid flow forces exerted on the elastic segment 3B. The reinforcing structure 22 may include a flange, a ring, a trumpet or a filter disposed on the open end or made integrally with the inlet.

In an embodiment of the disclosed high flow volume nasal irrigation device, at least one of the cap 2, the dip tube and the elastic segment 3B may be comprised of a purple material, a purple coloring and/or a purple covering configured as a color code for consumers to identify and differentiate the device for purchase and proper application. Since the advantages of the present disclosure distinctly set it apart from other nasal irrigation devices on the market, consumers will naturally want to continue their exclusive purchase of the disclosed device they have come to trust and rely upon for specific medicinal and hygienic applications. The color code as claimed herein allows consumers to avoid mistakes in purchasing other less advantageous and applicable nasal irrigators and to consistently identify and purchase the disclosed device by the purple color code.

FIG. 4A is a cross-sectional view of a straight walled socket taken through the diameter of the elastic segment in accordance with an embodiment of the present disclosure. The tube segment 3A is shown with an inside diameter in broken lines prior to making a connection with the elastic segment 3B. The elastic segment 3B includes a bore 25 approximating the outside diameter of the tube segment 3A but slightly smaller to support a snug elastic fit.

FIG. 4B is a cross-sectional view of the straight walled socket after the tube segment 3A is inserted therein in accordance with an embodiment of the present disclosure. A discontinuity 26 may be seen between the end of the segment 3A and the bottom of the straight walled socket. The discontinuity 26 may create turbulence in the fluid flow through the dip tube and slow down fluid velocity and weaken the fluid flow ejected from the device into a user's nostril.

FIG. 4C is a cross-sectional view of a pocket socket taken through the diameter of the elastic segment in accordance with an embodiment of the present disclosure. The elastic segment 3B includes a pocket 27, a taper 28 and a bore 25. The taper forms a transition from the bore 25 diameter to the pocket 27 diameter. The pocket 27 is designed to have a diameter larger than the diameter of the bore 25 and therefore larger than the inside diameter of the elastic segment 3B.

FIG. 4D is a cross-sectional view of the pocket socket after the tube segment 3A is inserted therein in accordance with an embodiment of the present disclosure. The circumferential transition 30 between the tube segment 3A and the elastic segment 3B shows a snug stretched fit with no discontinuity between the inside diameters of both segments. Therefore, an end of the elastic segment 3B is configured into a socket to receive the dip tube in a stretched fit connection, a pocket portion 27 of the socket proximal to the elastic segment 3B is configured to have an inside diameter larger than an inside diameter of another portion of the socket distal to the segment allowing a substantially turbulence free transition between the two segments for a smooth transition between segments and more efficient nasal irrigation.

Figure 5:
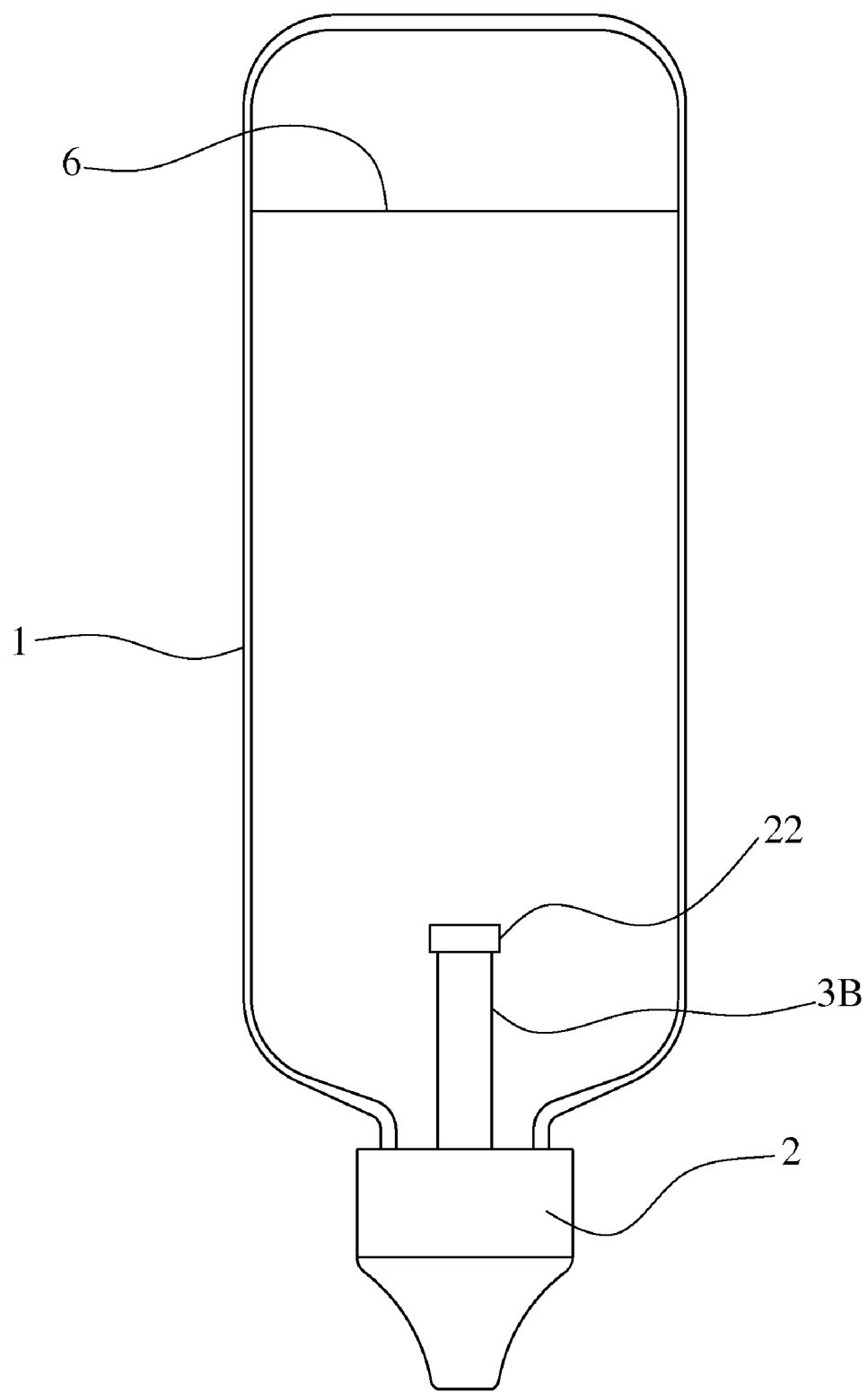
FIG. 5 is a side elevational view of a transparent inverted high flow volume nasal irrigation device for alternating pulsatile and continuous fluid flow in accordance with an embodiment of the present disclosure.

FIG. 5 is a side elevational view of an inverted high flow volume nasal irrigation device for alternating pulsatile and continuous fluid flow in accordance with an embodiment of the present disclosure. The inverted device depicts the squeeze bottle 1, a cap 2, an elastic segment 3B, a reservoir 6, and an inlet structure 22. The inverted configuration comprises all the pulsatile and continuous fluid flow characteristics of the device of FIG. 2 with the advantages of shorter dip tube length and a potentially shorter squeeze bottle 1. The shorter dip tube length may increase pulsation frequencies by up to three times the pulsation frequencies of the non-inverted configuration. The inverted nasal irrigation device depicted and disclosed may also have advantages acting as a second reservoir in second reservoir applications as discussed below involving a conveyance tube.

Embodiments of the disclosed device also provide non-pulsating continuous stream irrigation if the velocity of the fluid flow is maintained below a critical level initiating pulsation. The flow rate of this continuous stream may be controlled by the user over a wide range. If desired by the user, the disclosed device may produce a continuous stream flow rate which is significantly higher than the time averaged flow rate of the device in pulsation mode.

When the disclosed device is operated in the pulsation mode, aka pulsation state, the disclosed pulse generating mechanism may act as a flow control to maintain or even reduce flow in response to increases in bottle or chamber pressure beyond that required to initiate pulsation. With the device in pulsatile mode, increases in squeeze pressure from the user may cause an increase in pulsation amplitude while regulating flow rate to a safe and effective level.

Figure 6A:
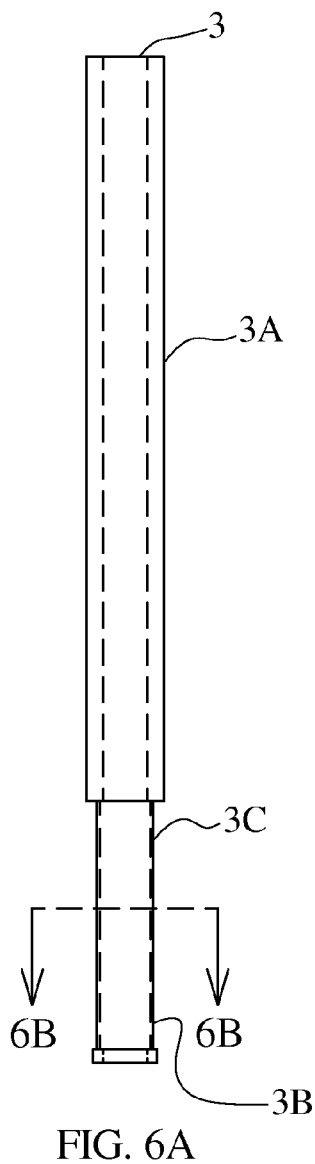
FIG. 6A is a longitudinal view of a tube with an arcuate elastic segment in accordance with an embodiment of the present disclosure.

FIG. 6A is a longitudinal view of a tube 3 with an arcuate elastic segment in accordance with an embodiment of the present disclosure. The elastic segment 3B may also comprise arcuate cross sections including oval, cylindrical and elliptical configurations. A cross-section 6B-6B is taken through the elastic segment to illustrate an oval embodiment of the elastic segment 3B.

Figure 6C:
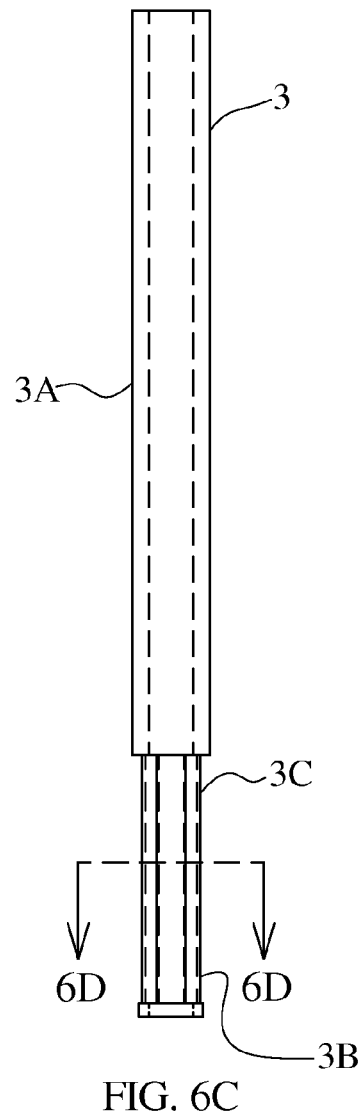
FIG. 6C is a longitudinal view of tube with a polygonal elastic segment in accordance with an embodiment of the present disclosure.
Figure 6E:
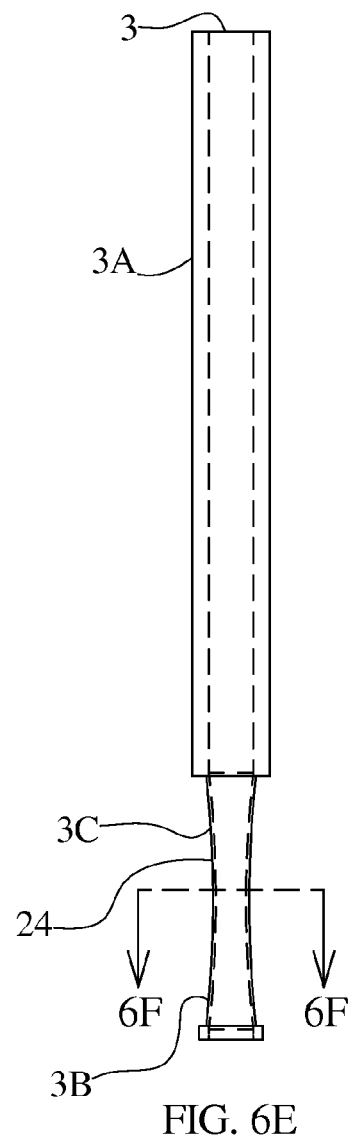
FIG. 6E is a longitudinal view of a tube with a venturi elastic segment in accordance with an embodiment of the present disclosure.
Figure 6B:
FIG. 6B is a cross-sectional view of the elastic segment in FIG. 6A in accordance with an embodiment of the present disclosure.

FIG. 6B is a cross-sectional view of the elastic segment in FIG. 6A in accordance with an embodiment of the present disclosure. Also, an oval cross section may cause the initiation of pulsation to occur at lower flow velocities because there is no symmetric hoop stress to overcome before the tube begins to buckle in response to the pressure differential.

FIG. 6C is a longitudinal view of a tube 3 with a polygonal elastic segment in accordance with an embodiment of the present disclosure. Cross sections such as square, rectangular and also higher numbering geometries such as pentagonal, octagonal and so forth are embodied herein. A cross-section 6D-6D is taken through the elastic segment to illustrate a hexagonal embodiment of the elastic segment 3B.

Figure 6D:
FIG. 6D is a cross-sectional view of the elastic segment of FIG. 6C in accordance with an embodiment of the present disclosure.

FIG. 6D is a cross-sectional view of the elastic segment of FIG. 6C in accordance with an embodiment of the present disclosure. Bending and closing or opening of the pulsatile portion may occur at any of the vertices of the hexagon illustrated in cross-section.

FIG. 6E is a longitudinal view of a tube 3 with a venturi elastic segment in accordance with an embodiment of the present disclosure. A cross-section 6F-6F is taken through the elastic segment to illustrate this embodiment of the elastic segment 3B. The depicted embodiment of the present disclosure comprises a pre-formed venturi in the elastic segment 3B. A pre-formed venturi 24 may increase pressure differential for a given flow rate and thus lower the pressure necessary to initiate pulsation.

Figure 6F:
FIG. 6F is a cross-sectional view of the elastic segment of FIG. 6E in accordance with an embodiment of the present disclosure.

FIG. 6F is a cross-sectional view of the elastic segment of FIG. 6E in accordance with an embodiment of the present disclosure. A venturi 24 embodiment may also require less pressure to sustain the periodic closing and reopening of the pulsatile portion 3C in the elastic segment 3B. Therefore, once pulsation has initiated, the elastic restoring force intrinsic to the pulsatile portion 3C may reopen the tube and the cycle of closing and re-opening may continue at a frequency controlled by the user as discussed below. Boundaries for the frequency of operation may be set by the design of physical properties of the pulsatile portion including wall thickness of the portion, elasticity of the portion, an inside diameter of the portion and the length of the dip tube.

Figure 7:
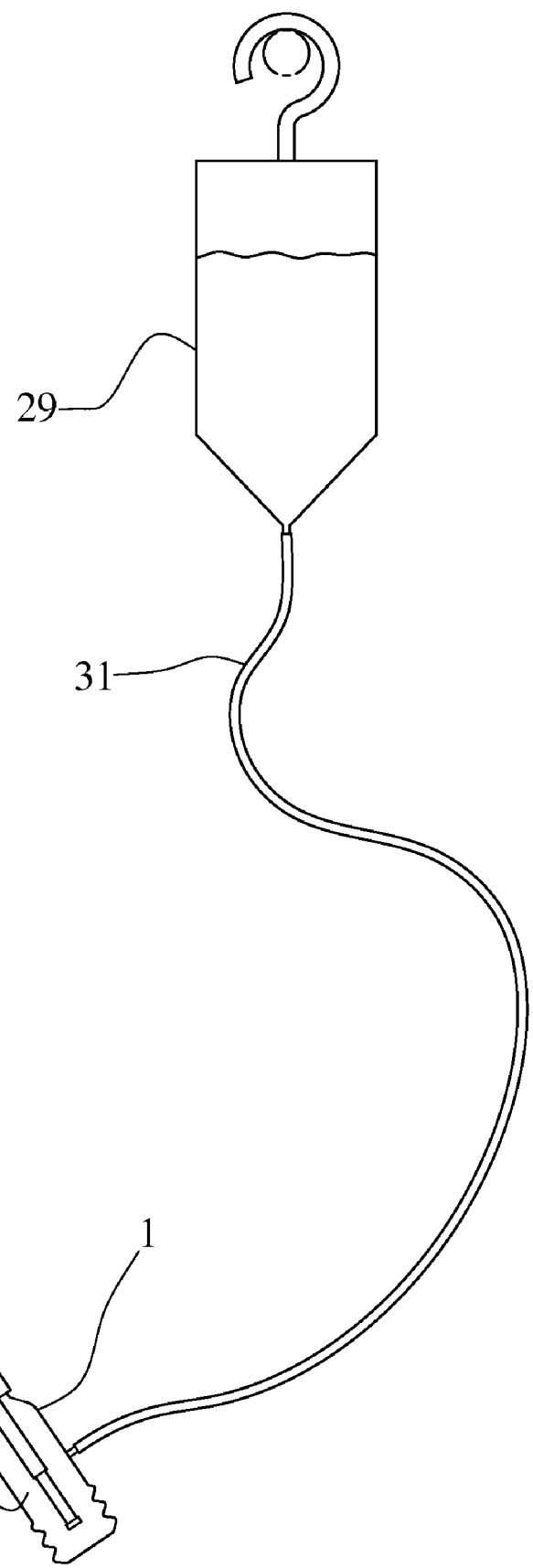
FIG. 7 is a depiction of a second reservoir device in accordance with an embodiment of the present disclosure.

FIG. 7 is a depiction of a second reservoir device in accordance with an embodiment of the present disclosure. Another embodiment of the disclosed high flow volume nasal irrigation device may include a second reservoir 29 of liquid located at a height above the user and the first reservoir 6. The second reservoir 29 may be configured to create a pressure from a volume of liquid at a predetermined height. The disclosed embodiment may also include a conveyance tube 31 arranged to convey fluid from the second reservoir 29 into the chamber 1 through an effective column of fluid. This embodiment and like embodiments may therefore preclude a user squeezing the chamber 1 since the derived pressure necessary to induce pulsatile flow is created by the second reservoir 29 and the column of liquid through the conveyance tube 31. A valve may be configured in the fluid path from the second reservoir 29 to the chamber 1 to control the flow of fluid into the chamber 1.

Figure 8:
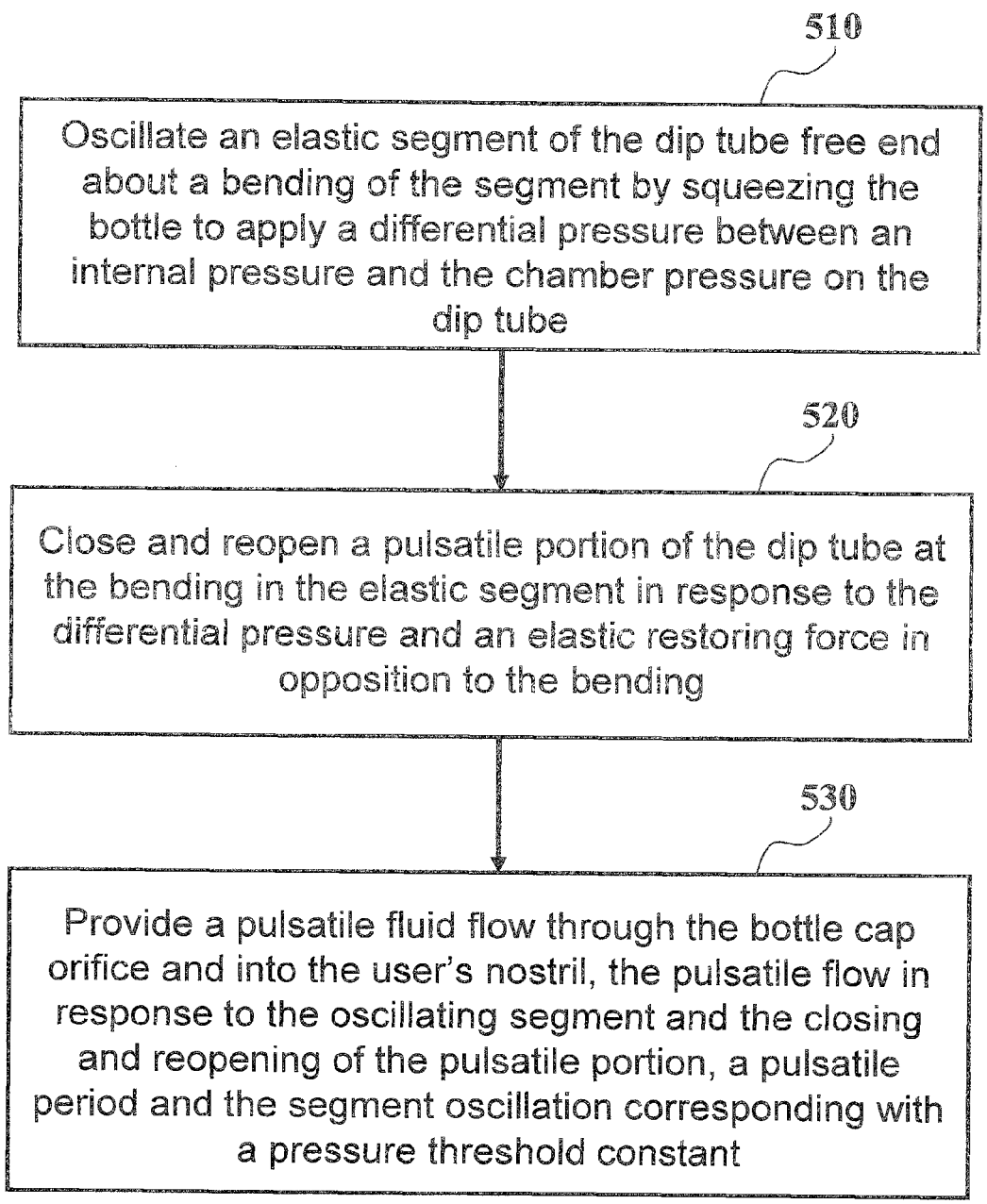
FIG. 8 is a flow chart of a method of alternating pulsatile and continuous fluid flow through a high flow volume nasal irrigation device in accordance with an embodiment of the present disclosure.

FIG. 8 is a flow chart of a method of ejecting a high flow volume pulsatile nasal irrigation rinse in accordance with an embodiment of the present disclosure. Embodiments may include methods of ejecting a high flow volume nasal irrigation rinse by squeezing a deformable bottle containing a liquid and thereby urging the liquid through a dip tube in the bottle out a bottle cap orifice placed adjacent at least one of a user's nostrils. One embodied method includes 510 oscillating an elastic segment of the dip tube free end about a bending of the segment by squeezing the bottle to apply a differential pressure between an internal pressure and the chamber pressure on the dip tube. The method also includes 520 closing and reopening a pulsatile portion of the dip tube at the bending in the elastic segment in response to the differential pressure and an elastic restoring force in opposition to the bending. The method further includes 530 providing a pulsatile fluid flow through the bottle cap orifice and into the user's nostril, the pulsatile flow in response to the oscillating segment and the closing and reopening of the pulsatile portion, a pulsatile period and the segment oscillation corresponding with a pressure threshold constant.

Figure 9:
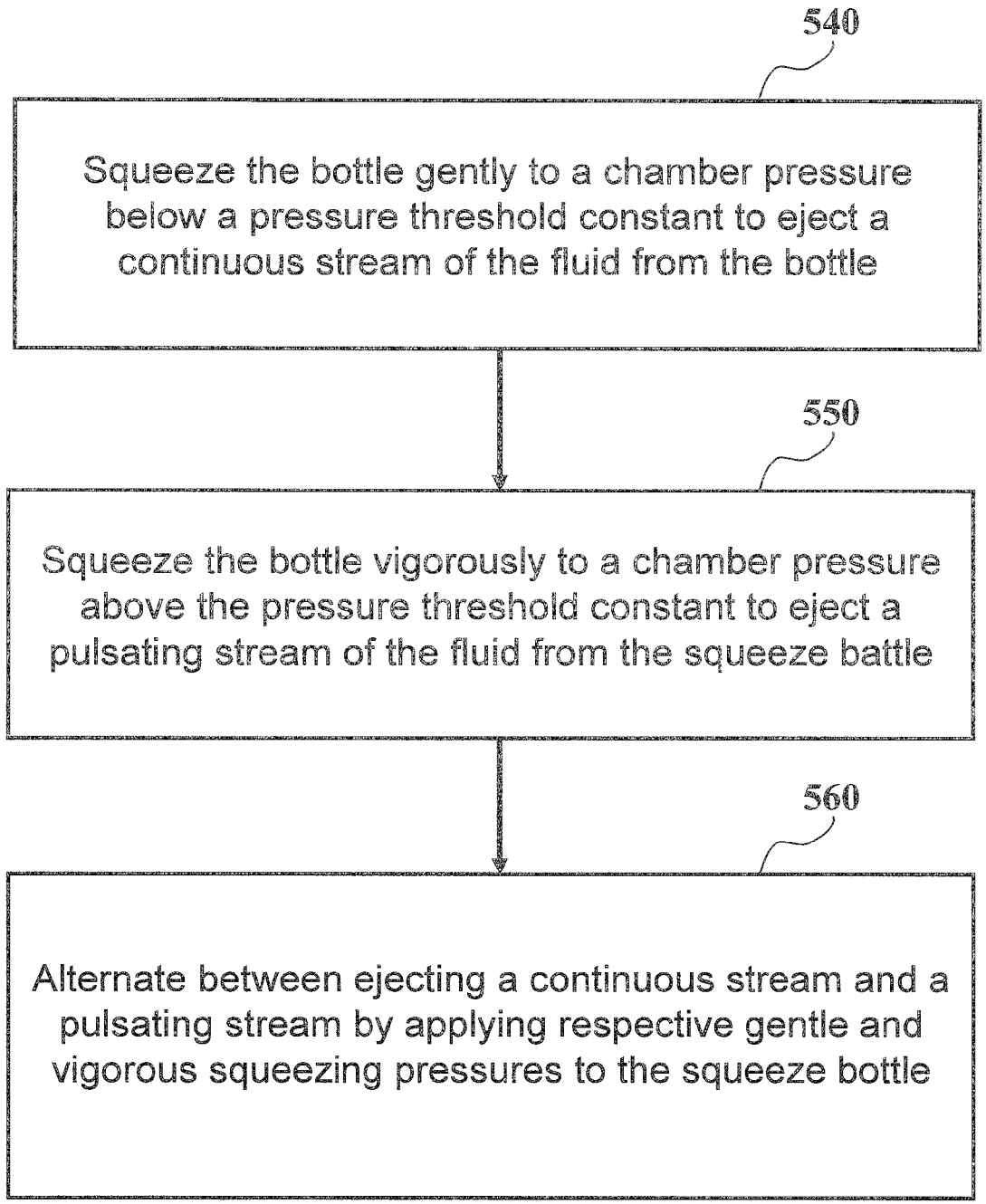
FIG. 9 is a flow chart of a method in accordance with an embodiment of the present disclosure.

FIG. 9 is a flow chart of a method of alternating pulsatile and continuous flow through a high flow volume nasal irrigation device in accordance with an embodiment of the present disclosure. An embodiment of the method of ejecting a high flow volume nasal irrigation rinse of above, further comprises 540 squeezing the bottle gently to a chamber pressure below a pressure threshold to eject a continuous stream of the fluid from the bottle and 550 squeezing the bottle vigorously to a chamber pressure above the pressure threshold to eject a pulsating stream of the fluid from the squeeze bottle. The disclosed embodiment further includes 560 alternating between ejecting a continuous stream and a pulsating stream by applying respective gentle and firm or vigorous squeezing pressures to the squeeze bottle.

In support of the above operation and procedure of the disclosed nasal irrigation device, a user may remove the cap assembly, including the dip tube, from the bottle. The user fills the squeeze bottle to a desired level with either previously prepared rinsing solution or with water preferably at body temperature. If filled with water, the user may add a prepackaged solute resulting in the desired solution when agitated. After screwing the cap assembly on the bottle, the user may position herself or himself over a basin and align and lightly press the cap orifice against one nostril to obtain a seal with the nostril. The user then applies a respective squeeze pressure to the bottle in order to force a continuous or pulsatile fluid flow into the nose and sinus cavities. The user may perform the procedure on the other nostril blowing his or her nose between sequences.

An embodiment of the method of ejecting a high flow volume nasal irrigation rinse may further comprise configuring the pressure threshold constant as a function of at least a hoop stress buckling limit of the pulsatile portion and varying the pressure threshold constant by varying at least one of a wall thickness of the portion, an elasticity or durometer of the portion, an inside diameter of the portion and a length of the dip tube.

Another embodiment of the method of ejecting a high flow volume nasal irrigation rinse may further comprise varying an oscillatory frequency of the pulsating stream of fluid by dynamically varying at least one of the manual pressure applied to the squeeze bottle and statically varying a physical property of the elastic portion including a wall thickness of the elastic portion, an inside diameter of the elastic portion and a length of the segmented dip tube. The disclosed nasal irrigation device may be operated at a nominal oscillatory frequency of 10 Hertz to 20 Hertz by varying the manual chamber or squeeze pressure and the maintenance pressure applied to the squeeze bottle. Therefore, the operating frequency controlled by the user may resonate with the natural beat of the nasal cilia. The user may also generate other pulsatile frequencies operating the disclosed device as needed to achieve medicinal and hygienic results.

Figure 10:
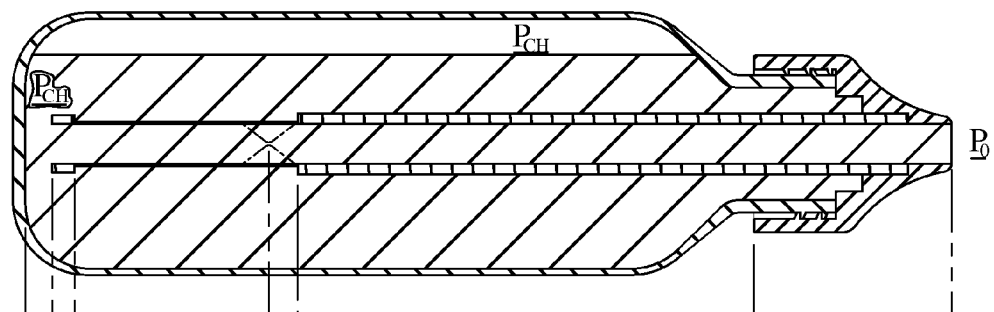
FIG. 10 is a depiction of a nasal irrigation device in a horizontal position in accordance with an embodiment of the present disclosure.

FIG. 10 is a depiction of a nasal irrigation device in a horizontal position in accordance with an embodiment of the present disclosure. The depicted embodiment has been tipped horizontally so that phantom lines may be used to guide correspondences of position to FIG. 11 below. Assuming that the pressure within the chamber, Pch is held constant and the pressure external to the device, Po is also held constant and the pressure difference between Pch and Po is assumed to be higher than the threshold constant required to cause pulsation.

Figure 11:
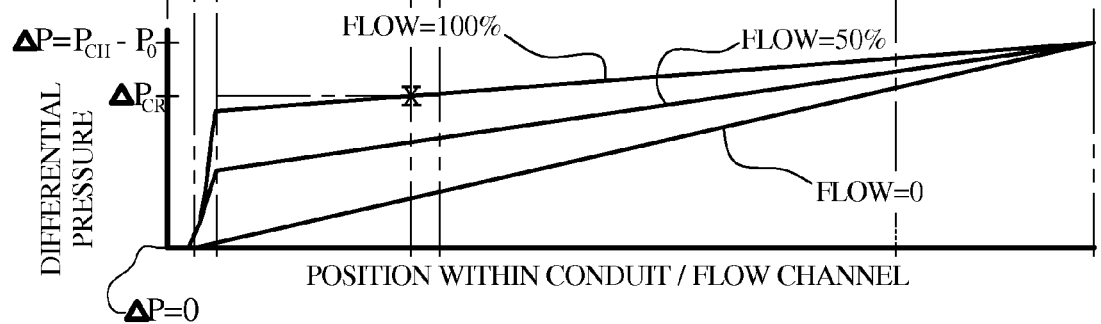
FIG. 11 is a plot of the pressure differential acting across the tube wall at any point along the length of the tube in accordance with an embodiment of the present disclosure.

FIG. 11 is a plot of the pressure differential acting across the tube wall at any point along the length of the tube. These curves were generated by subtracting the pressure within the tube from the pressure acting on the exterior of the tube, Pch for three different flow levels. It can be seen from this plot that the portion of the elastic segment that is furthest downstream will be acted upon by the greatest pressure differential thus causing the pulsatile section to be in a fixed location. This plot depicts a critical pressure $\Delta Pcr$ which is that pressure differential sufficient to cause a buckling collapse of the elastic segment and a bending of the tube free end about the buckling. This buckling condition is met at the intersection of the 100% flow curve and $\Delta Pcr$ which is marked with an "X" and which corresponds (following the phantom line up from the "X") to the physical location of the pulsatile portion.

Figure 12:
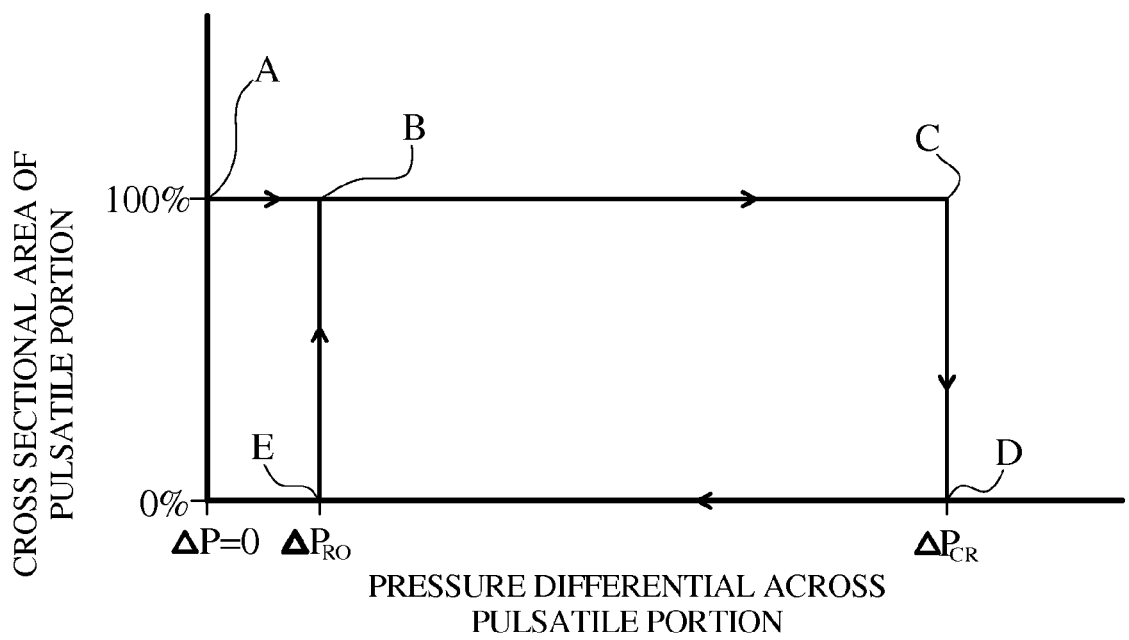
FIG. 12 is a depiction of the several modes of the nasal irrigation device as a function of the pressure differential across the elastic segment versus the cross sectional area of the elastic segment in accordance with an embodiment of the present disclosure.

FIG. 12 is a depiction of the several modes of the nasal irrigation device as a function of the pressure differential across the pulsatile portion versus the cross sectional area of the pulsatile portion in accordance with an embodiment of the present disclosure. The horizontal axis labeled pressure differential should also be understood to roughly correlate with flow velocity. At the initiation of chamber pressure such as would be generated by a squeeze, the device is operating at point A. In this condition the pulsatile section is fully open and flow is just beginning. With time the mode of operation would be that of a point on the line between A and C. If the squeeze pressure on the bottle is not sufficient to exceed the critical chamber pressure required to cause pulsation then the operation would stabilize at a point intermediate along line A-C, with the pulsatile section remaining fully open and a steady state flow rate being eventually established. If the squeeze pressure applied and maintained is sufficient to exceed the critical chamber pressure required to cause pulsation, then the flow and differential pressure would quickly increase to point C and the critical pressure differential $\Delta Pcr$ would be exceeded and the pulsatile segment would buckle to closure (0% area) and the tube free end would bend about the buckle. This would occur by a near instantaneous state change to point D. With the tube closed and flow stopped the state moves to a point E at which the differential pressure drops to a point low enough (Pro) that the elastic restoring forces present in the elastomeric tube re-open the tube fully and the tube free end returns or oscillates back to its initial position. This occurs rapidly, moving the state back to B. The cycle will continue to advance from B to C to D to E and repeat back to B as long as the user choses to maintain a Pch above the critical level. Of the transitions between states all take a small portion of the total cycle time except for that which occurs along line A-C due to the fact that A-C requires the acceleration of the column of water by the relatively low drive (chamber) pressure.

Figure 13:
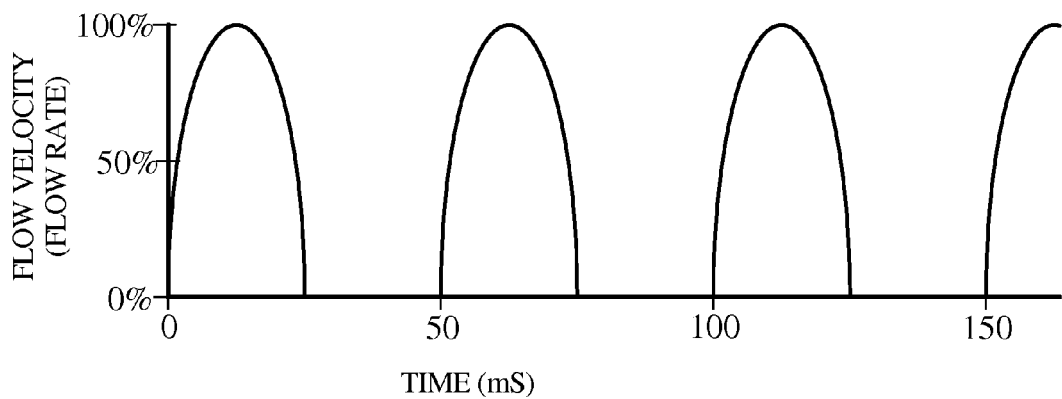
FIG. 13 depicts variations in flow velocity over time for prior art nasal irrigation devices having pulsatile flow.

FIG. 13 depicts variations in flow velocity over time for prior art nasal irrigation devices having pulsatile flow. Devices characterized by the depiction herein may be operated by a fixed displacement piston pump and therefore have the form of a rectified sine wave. Fixed displacement piston pumps are carryover technology from their use as high pressure oral cleaners and are therefore not optimized for effectiveness in cleaning nasal passages or sinuses.

Figure 14:
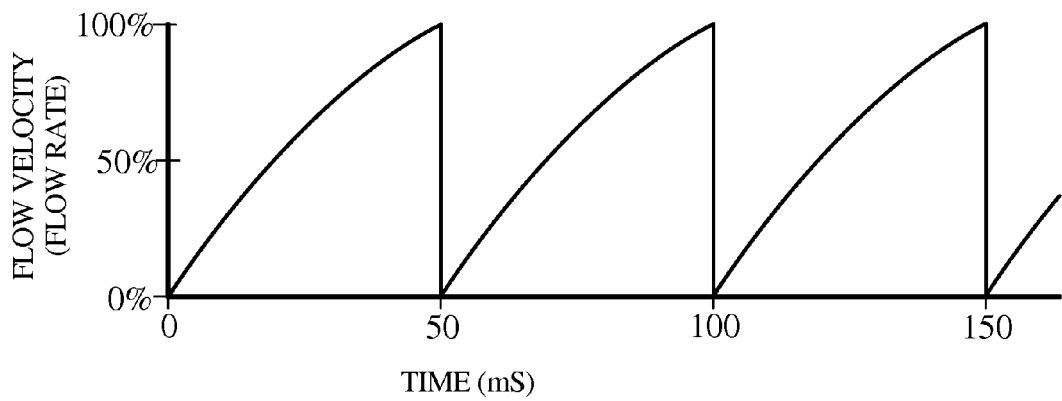
FIG. 14 depicts variations in flow velocity over time of a nasal irrigation device tuned to a 20 Hz frequency in accordance with an embodiment of the present disclosure.

FIG. 14 depicts variations in flow velocity over time of a nasal irrigation device tuned to a 20 Hz frequency in accordance with an embodiment of the present disclosure. The depiction shows variations in flow velocity over time, with the assumption that the device has been tuned to the preferred 20 Hz frequency, however, the device may also be tuned to slower or faster frequencies by adjusting the differential pressure and design parameters. Within each cycle the longest portion of time is spent accelerating the column of liquid up to the velocity necessary to cause a critical pressure differential (labeled as 100%). This is a time constant phenomenon, thus the asymptotically curving line followed by a very rapid cessation of flow after which the fluid flow resumes. This rapid closure is beneficial in that it creates inertial cleaning effects within the nasal passages and sinuses. This rapid closure and its benefits are markedly absent in the characterization depicted in FIG. 13.

The disclosed device may also be used as a general purpose lavage in the therapeutic washing of bodily orifices, organs, wounds and abrasions. Advantages of the disclosed sinus and nasal irrigation device include the ability to provide the best benefits of the simple squeeze bottle irrigators and simultaneously provide the best benefits of the complex electromechanical irrigators while avoiding any of the negatives of either of these classes of devices. Specifically, advantages of the disclosed device include: a very low manufacturing cost, comparable to that of a squeeze bottle irrigator, a very low part count—requires only 3 to 4 separate manufactured components, continuous stream or pulsatile irrigation from the same device without need for the user to reconfigure the device, a continuous stream which the user may vary in strength from minimal flow up to a flow rate which equals or exceeds currently available irrigation devices, a pulsatile stream which the user may vary in strength from weak through a pulsation amplitude which exceeds that of currently available pulsatile irrigation devices, improved cleansing action, improved distribution of medicated solutions, improved ability to project solution into sinus cavities, improved ability to stimulate nasal cilia, inherent flow regulation which allows the user to squeeze firmly without risking exposure to harmful flow rates, simple and intuitive operation with no external controls, no need for power cords, hoses, or other encumbrances, open construction with no confined area prone to pooling allows very easy and effective rinsing and air drying of all surfaces after use, reduction in the possibility of mold colonization through open construction and a cap shape which allows safe and easy use while effectively directing the flow stream into the correct areas of the nose.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A high flow volume nasal irrigation device, comprising:
   a) a segmented tube having a free end extending inside a chamber and an end extending outside the chamber, the tube configured to convey a liquid under an elevated chamber pressure from a reservoir therein to a lower pressure outside the chamber;
   b) an elastic segment configured at the free end of the tube, the free end configured to oscillate about a bending of the segment in response to a differential pressure between an internal pressure and the chamber pressure, the segment having an elastic restoring force in opposition to the bending; and
   c) a pulsatile portion of the elastic segment configured to close at the segment bending and to reopen under the elastic restoring force and to thus generate a periodic pulsatile fluid flow through the tube with a period corresponding to the elastic segment oscillation.

2. The high flow volume nasal irrigation device of claim 1, further comprising a predetermined location for the bending of the elastic segment where the differential pressure across the segment overcomes a hoop stress buckling limit of the segment and closes the pulsatile portion, the differential pressure determined in part by a decrease of the internal pressure in the segment resulting from an elevated fluid velocity therein.

3. The high flow volume nasal irrigation device of claim 1, wherein the pulsatile portion is configured to reopen to its original cross section at a predetermined bending location where the elastic restoring force intrinsic to the portion configuration overcomes the differential pressure across the segment, the differential pressure determined in part by an increase of the internal pressure in the segment resulting from a decrease of the fluid velocity therein.

4. The high flow volume nasal irrigation device of claim 1, wherein the tube free end comprises an inlet structure configured to generate an initial fluid pressure drop across the inlet to locate the pulsatile portion in the elastic segment and configured to prevent the free end from collapsing.

5. The high flow volume nasal irrigation device of claim 1, further comprising:

a) a second reservoir of liquid located at a height above the first reservoir, the second reservoir configured to create the chamber pressure from a volume of liquid at a predetermined height; and
   b) a conveyance tube configured to convey the fluid from the second reservoir into the chamber and introduce an increase in pressure in the chamber.

6. The high flow volume nasal irrigation device of claim 1, wherein a length of the pulsatile portion along the elastic segment is substantially equal to the inside diameter of the segment.

7. The high flow volume nasal irrigation device of claim 1, wherein a wall thickness of the elastic segment extends only for a length between 1 and 10 times an inside diameter of the segment.

8. A high flow volume nasal irrigation device, comprising:
   a) a squeeze bottle configured to elastically deform in response to a manually applied pressure from a user's thumb and fingers and thus pressurize the liquid therein, the squeeze bottle comprising an open end and an interior;
   b) a segmented dip tube having a free end extending into the squeeze bottle, the free end comprising an inside diameter and an inlet structure configured to generate a predetermined pressure drop in a fluid flow in the tube and to prevent the free end from collapsing;
   c) an elastic segment at the free end configured to oscillate about a bending in response to a differential pressure between an internal pressure and the applied pressure, the segment comprising a pulsatile portion which closes and reopens at the bending to generate a pulsatile fluid flow with a period corresponding to the elastic segment oscillation; and
   d) a removable cap disposed on the squeeze bottle open end, the cap comprising an orifice and a bore coaxial with the orifice, the bore configured to receive the dip tube second end and match the orifice with the inside diameter of the dip tube.

9. The high flow volume nasal irrigation device of claim 8, wherein an end of the elastic segment is configured into a socket to receive the dip tube in a stretched fit connection, a pocket portion of the socket proximal to the segment configured to have an inside diameter larger than an inside diameter of another portion of the socket distal to the segment.

10. The high flow volume nasal irrigation device of claim 8, further comprising a pre-formed venturi in the elastic segment configured to lower the egressing fluid pressure therein and facilitate the collapse of the elastic segment.

11. The high flow volume nasal irrigation device of claim 8, wherein the elastic segment is comprised of an elastomeric deformable material having a low durometer and at least one of an arcuate cross section and any polygonal cross section.

12. The high flow volume nasal irrigation device of claim 8, wherein the elastic segment comprises a 6 mm (0.24 inches) nominal inside diameter and is no smaller than 3 mm (0.12 inches) in diameter and no greater than 8 mm (0.32 inches) in diameter.

13. The high flow volume nasal irrigation device of claim 8, wherein the elastic segment is comprised of a wall thickness no smaller than 0.15 mm (0.006 inches) and no greater than 0.69 mm (0.027 inches).

14. The high flow volume nasal irrigation device of claim 8, wherein the elastic segment is further configured to collapse when subjected to an externally applied pressure differential of 2.07 kPa (0.3 psi) to 13.80 kPa (2.0 psi) and return to its original form when the pressure differential is reduced to less than 1.72 kPa (0.25 psi).

15. The high flow volume nasal irrigation device of claim 8, wherein at least one of the cap, the dip tube and the elastic segment are comprised of a purple material, a purple coloring and/or a purple covering configured as a color code for consumers to identify and differentiate the device for purchase and proper application.

16. A method of ejecting a high flow volume nasal irrigation rinse by squeezing a deformable bottle containing a fluid and thereby urging the fluid into a dip tube free end in the bottle and through a segmented dip tube and out a bottle cap orifice placed adjacent at least one of a user's nostrils, comprising:
    a) oscillating an elastic segment of the dip tube free end about a bending of the segment by squeezing the bottle to apply a differential pressure between an internal pressure and the squeeze pressure on the dip tube;
    b) closing and reopening a pulsatile portion of the dip tube at the bending in the elastic segment in response to the differential pressure and an elastic restoring force in opposition to the bending; and
    c) providing a pulsatile fluid flow through the bottle cap orifice and into the user's nostril, the pulsatile flow in response to the oscillating segment and the closing and reopening of the pulsatile portion, a pulsatile period and the segment oscillation corresponding with a pressure threshold constant.

17. The method of ejecting a high flow volume nasal irrigation rinse of claim 16, further comprising:
    a) squeezing the bottle gently to a chamber pressure below the pressure threshold constant to eject a continuous stream of the fluid from the bottle;
    b) squeezing the bottle vigorously to a chamber pressure above the pressure threshold constant to eject an oscillatory pulsating stream of the fluid from the bottle; and
    c) alternating between ejecting a continuous fluid stream and a pulsating fluid stream by alternating the respective gentle and vigorous squeezings.

18. The method of ejecting a high flow volume nasal irrigation rinse of claim 16, further comprising configuring the pressure threshold constant as a function of at least a hoop stress buckling limit of the pulsatile portion.

19. The method of ejecting a high flow volume nasal irrigation rinse of claim 16, further comprising varying the pressure threshold constant by varying at least one of a wall thickness of the portion, an elasticity of the portion, an inside diameter of the portion and a length of the dip tube.

20. The method of ejecting a high flow volume nasal irrigation rinse of claim 16, further comprising varying an oscillatory frequency and period of a pulsating stream of fluid ejected from the bottle by varying the manual pressure applied to the squeeze bottle.

* * * * *